United States Patent
Park et al.

(10) Patent No.: US 11,517,394 B2
(45) Date of Patent: Dec. 6, 2022

(54) METHOD FOR CALIBRATION OF LASER TARGETING PROJECTOR AND C-ARM IMAGE, RECORDING MEDIUM FOR PERFORMING THE SAME AND LASER SURGICAL GUIDANCE SYSTEM INCLUDING CALIBRATION TOOL

(71) Applicant: KYUNGPOOK NATIONAL UNIVERSITY INDUSTRY-ACADEMIC COOPERATION FOUNDATION, Daegu (KR)

(72) Inventors: Ilhyung Park, Daegu (KR); Hyunwoo Lee, Daegu (KR); Sanghyun Joung, Daegu (KR); Chulwoo Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 744 days.

(21) Appl. No.: 16/474,985

(22) PCT Filed: Nov. 29, 2017

(86) PCT No.: PCT/KR2017/013769
§ 371 (c)(1),
(2) Date: Jun. 28, 2019

(87) PCT Pub. No.: WO2018/124499
PCT Pub. Date: Jul. 5, 2018

(65) Prior Publication Data
US 2019/0321125 A1    Oct. 24, 2019

(30) Foreign Application Priority Data
Dec. 29, 2016   (KR) .................. 10-2016-0181943

(51) Int. Cl.
*G06K 9/00*   (2022.01)
*A61B 17/00*  (2006.01)
(Continued)

(52) U.S. Cl.
CPC ............. *A61B 90/36* (2016.02); *G06T 7/30* (2017.01); *A61B 17/1703* (2013.01);
(Continued)

(58) Field of Classification Search
CPC .......... A61B 17/00; A61B 18/18; G06K 9/00
(Continued)

(56) References Cited

U.S. PATENT DOCUMENTS 5,676,673 A * 10/1997 Ferre ................. G01B 7/004
606/1
2014/0276108 A1* 9/2014 Vertikov ............. A61B 5/0066
600/478

(Continued)

FOREIGN PATENT DOCUMENTS

JP   2015-526231 A   9/2015
KR   10-0731052 B1   6/2007
(Continued)

OTHER PUBLICATIONS

Zhengyou Zhang, "A flexible new technique for camera calibration", IEEE Transactions on Pattern Analysis and Machine Intelligence, 22(11):11330-1334, 2000., Dec. 2, 1998, Microsoft Research, Redmond, WA.

*Primary Examiner* — Seyed H Azarian
(74) *Attorney, Agent, or Firm* — Novick, Kim & Lee PLLC; Jae Youn Kim

(57) ABSTRACT

Provided is a laser surgical guidance system including a C-arm fluoroscopy (hereinafter, C-arm) to identify a patient's condition and support a surgical plan and a laser targeting projector to project a line of the surgical plan
(Continued)

directly onto an affected part through a line projection module which generates a laser. The laser surgical guidance system may generate a particular laser pattern from the line projection module, transmit the particular laser pattern outputted from the line projection module through a calibration tool including a collimator having a particular orientation, calculate an extrinsic parameter of the calibration tool in a projection image having passed through the calibration tool, and convert coordinates of the C-arm image into the line projection module coordinates using the extrinsic parameter.

16 Claims, 8 Drawing Sheets

(51) Int. Cl.
    *A61B 90/00*       (2016.01)
    *G06T 7/30*        (2017.01)
    *A61B 17/17*       (2006.01)
    *A61B 90/13*       (2016.01)

(52) U.S. Cl.
    CPC ..... *A61B 90/13* (2016.02); *A61B 2017/00725* (2013.01); *A61B 2090/366* (2016.02); *A61B 2090/373* (2016.02); *A61B 2090/376* (2016.02); *A61B 2090/3764* (2016.02)

(58) Field of Classification Search
    USPC ....... 382/100, 103, 106, 128–133, 168, 173, 382/181, 199, 209, 214, 254, 276, 286, 382/291, 295, 305; 378/4, 21; 600/1, 600/478; 606/1, 46
    See application file for complete search history.

(56) References Cited

U.S. PATENT DOCUMENTS

| | | | |
|---|---|---|---|
| 2017/0238807 A9* | 8/2017 | Vertikov | A61B 5/1079 |
| 2019/0000564 A1* | 1/2019 | Navab | A61B 34/30 |
| 2020/0305980 A1* | 10/2020 | Lang | A61B 34/10 |

FOREIGN PATENT DOCUMENTS

| | | |
|---|---|---|
| KR | 10-2010-0112309 A | 10/2010 |
| KR | 10-2013-0121514 A | 11/2013 |
| KR | 10-2015-0125069 A | 11/2015 |
| KR | 10-2016-0007700 A | 1/2016 |

* cited by examiner

METHOD FOR CALIBRATION OF LASER TARGETING PROJECTOR AND C-ARM IMAGE, RECORDING MEDIUM FOR PERFORMING THE SAME AND LASER SURGICAL GUIDANCE SYSTEM INCLUDING CALIBRATION TOOL

TECHNICAL FIELD

The present disclosure relates to a method for calibration of a laser targeting projector and a C-arm image, a recording medium for performing the same and a laser surgical guidance system including a calibration tool, and more particularly, to a method for calibration of a laser device for marking a surgical plan in a C-arm image onto an affected part and a calibration tool therefor.

BACKGROUND ART

In case that a surgical plan is made using an imaging device, it is difficult to perform a surgery as planned in the real surgical field. For example, in osteotomy, when an osteotomy is planned to be done 5 cm inferior to the knee joint, surgery needs to be performed with 5 cm incision made using the ruler at the real knee exposed through skin incision. However, there may be a huge difference between the real surgery and the planned one depending on the location and angle of the ruler.

Particularly, in the case of the technique for marking the site of perforation at surgery using a writing tool in reliance on the manual operation of the medical staff, especially when perforation is needed, because the medical staff has to rely on a 2D image of a C-arm fluoroscopy, it fails to provide critical information about whether to insert a surgical instrument vertically or obliquely into a target affected part inside the patient's skin. Therefore, surgery is performed relying on the surgical experience or intuition of the medical staff.

Moreover, surgery outcome in an operation room greatly depends on the surgical experience of the medical staff involved in the surgery or their medical ability to interpret the affected part image information, and thus in the case of the medical staff having so little surgical experience, a considerable length of continuous preparation and training period is required for accurate surgery, resulting in the increased labor and material costs required for training.

Accordingly, guidance for accurately performing a surgery as planned is required. The conventional art involves obtaining an image of a patient using machine such as Computed Tomography (CT), magnetic resonance (MR) equipment, installing a marker at a predetermined part of the patient such as a leg in an operation room (the marker is an auxiliary instrument for matching the coordinates), and calibrating (calibrating coordinates) an image captured through MRI in the operation room using the corresponding marker.

Accordingly, two processes, namely, placing the marker on the patient's body and matching between the marker and the image, are required, and thus the surgical procedure is complex and it is impossible to provide real-time guidance. Additionally, imprecise matching between the marker and the image may adversely affect the surgical operation requiring high-level accuracy.

Particularly, in orthopedic surgeries, surgery is often performed after identifying the condition of a bone using a mobile C-arm fluoroscopy (hereinafter, C-arm) and making a surgical plan for cutting and reshaping of the bone. Currently, to this end, a k-wire (a stainless-steel wire) is placed at an affected part, a C-arm image is captured, and a surgical plan is made taking into account the positions of the bone and the k-wire.

A laser targeting projector is used to mark the planned lines in the C-arm image directly onto the affected part, and accurate spatial calibration between the laser target device and the C-arm necessary to use the laser targeting projector is essential.

RELATED LITERATURES

Patent Literature 1 KR 10-1650620 B1

(Non-Patent Literature 1) Z. Zhang, "A flexible new technique for camera calibration", IEEE Transactions on Pattern Analysis and Machine Intelligence, 22(11):1330-1334, 2000

DISCLOSURE

Technical Problem

In this context, the technical problem of the present disclosure addresses the above-described issue, and therefore the present disclosure is directed to providing a laser surgical guidance system including a calibration tool.

The present disclosure is further directed to providing a calibration tool for performing a method for calibration of a laser targeting projector and a C-arm image.

The present disclosure is further directed to providing a method for calibration of a laser targeting projector and a C-arm image.

The present disclosure is further directed to providing a recording medium having recorded thereon a computer program for performing a method for calibration of a laser targeting projector and a C-arm image.

Technical Solution

To achieve the above-described object of the present disclosure, a laser surgical guidance system according to an embodiment includes a C-arm fluoroscopy (hereinafter, C-arm) to identify a patient's condition and support a surgical plan and a laser targeting projector to project a line of the surgical plan directly onto an affected part, and the laser targeting projector includes a line projection module which generates a laser, a calibration tool that is spaced apart a predetermined distance from the line projection module, and including a collimator having a particular orientation for transmitting a particular laser pattern outputted from the line projection module, and a calibration unit which calculates an extrinsic parameter of the calibration tool in a projection image having passed through the calibration tool, and converts coordinates of the C-arm image into the line projection module coordinates.

In an embodiment of the present disclosure, the calibration tool may include an light pattern matching unit including the collimator having the particular orientation for transmitting the particular laser pattern outputted from the line projection module, and a C-arm marker unit including bearing balls arranged in a matrix to calculate the extrinsic parameter of the calibration tool so that the laser pattern having passed through the collimator is recognizable in the projection image.

In an embodiment of the present disclosure, the collimator of the light pattern matching unit may be formed in an opening pattern, and the opening pattern may be formed at a predetermined angle.

In an embodiment of the present disclosure, the calibration tool may further include a screen formed between the light pattern matching unit and the C-arm marker unit to see the laser pattern having passed through the collimator.

In an embodiment of the present disclosure, the bearing balls may be arranged in a 6×9 matrix.

In an embodiment of the present disclosure, the calibration unit may derive a conversion matrix between the C-arm image coordinates and the line projection module coordinates using a preset intrinsic parameter of the C-arm and the extrinsic parameter of the calibration tool.

In an embodiment of the present disclosure, the calibration unit may match the coordinates of origin of the C-arm image coordinates and the line projection module coordinates.

In an embodiment of the present disclosure, the line projection module may further include at least one of an optical apparatus to project the line, a CMOS camera to simulate the C-arm and a sensor to measure a distance from an object.

In an embodiment of the present disclosure, the optical apparatus may include at least one of a Galvano-mirror, a MEMS mirror and a Diffuser lens.

To achieve another object of the present disclosure as described above, a calibration tool for performing a method for calibration of a laser targeting projector and a C-arm image according to an embodiment includes a light pattern matching unit spaced apart a predetermined distance from the laser targeting projector, and includes a collimator having a particular orientation for transmitting a particular laser pattern outputted from the laser targeting projector, a screen for seeing the laser pattern having passed through the collimator, and a C-arm marker unit including bearing balls arranged in a matrix to calculate an extrinsic parameter so that the laser pattern having passed through the screen is recognizable by a C-arm.

In an embodiment of the present disclosure, the collimator of the light pattern matching unit may be formed in an opening pattern, and the opening pattern may be formed at a predetermined angle.

In an embodiment of the present disclosure, the bearing balls may be arranged in a 6×9 matrix.

To achieve still another object of the present disclosure as described above, a method for calibration of a laser targeting projector and a C-arm image according to an embodiment in a laser surgical guidance system includes a C-arm to identify a patient's condition and support a surgical plan, and the laser targeting projector to project a line of the surgical plan directly onto an affected part through a line projection module which generates a laser includes generating a particular laser pattern from the line projection module, transmitting the particular laser pattern outputted from the line projection module through a calibration tool including a collimator having a particular orientation, calculating an extrinsic parameter of the calibration tool in a projection image having passed through the calibration tool, and converting coordinates of the C-arm image into the line projection module coordinates using the extrinsic parameter.

In an embodiment of the present disclosure, the method of converting the coordinates of the C-arm image into the line projection module coordinates using the extrinsic parameter may include deriving a conversion matrix between the C-arm image coordinates and the line projection module coordinates using a preset intrinsic parameter of the C-arm and the extrinsic parameter of the calibration tool.

In an embodiment of the present disclosure, the method of converting the coordinates of the C-arm image into the line projection module coordinates using the extrinsic parameter may include matching the coordinates of origin of the C-arm image coordinates and the line projection module coordinates.

In an embodiment of the present disclosure, the method for calibration of a laser targeting projector and a C-arm image may further include projecting the projection image having undergone calibration of the coordinates of the C-arm image and the line projection module coordinates directly onto the affected part.

To achieve yet another object of the present disclosure as described above, a computer-readable recording medium according to an embodiment has recorded thereon a computer program for performing the method for calibration of a laser targeting projector and a C-arm image.

Advantageous Effects

According to the method for calibration of a laser targeting projector and a C-arm image, it is possible to achieve accurate spatial calibration between the laser module and the C-arm using the calibration tool, thereby providing accurate laser guidance. Additionally, it is possible to indicate a variety of surgery information including osteotomy lines, needle trajectories, and pin insertion position and insertion angle, thereby achieving accurate surgery as planned, and reducing the likelihood of surgical errors and medical malpractice. Further, it is possible to achieve quick and accurate surgery according to the imaging plan while reducing the dose of radiation exposure to the surgeon.

DETAILED DESCRIPTION OF MAIN ELEMENTS

Figure 1:
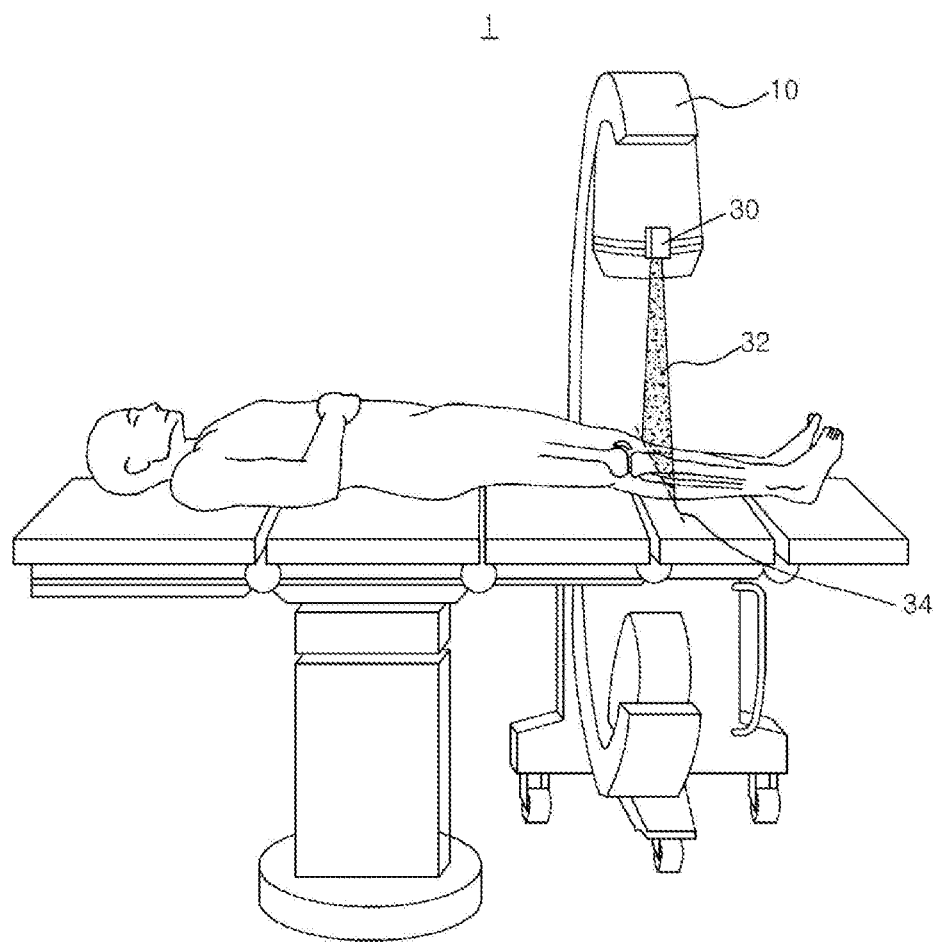
FIG. 1 is a conceptual diagram of a laser surgical guidance system according to an embodiment of the present disclosure.

1: Laser surgical guidance system
10: C-arm fluoroscopy
30: Laser targeting projector
32: Laser
34, 36, 38: Osteotomy line
50: Line projection module
70: Calibration tool
71: Light pattern matching unit
73: Screen
75: C-arm marker unit

Best Mode

The following detailed description of the present disclosure is made with reference to the accompanying drawings, in which particular embodiments for practicing the present disclosure are shown for illustration purposes. These embodiments are described in sufficient details for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, the preferred embodiments of the present disclosure will be described in more detail with reference to the accompanying drawings.

Figure 2:
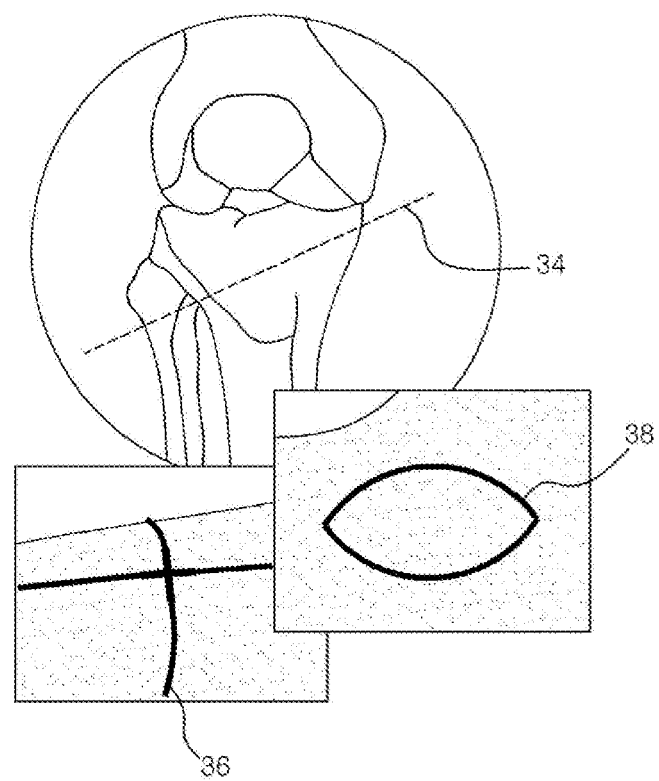
FIG. 2 is an exemplary diagram showing a projection image represented by a laser targeting projector of FIG. 1.

FIG. 1 is a conceptual diagram of a laser surgical guidance system according to an embodiment of the present disclosure. FIG. 2 is an exemplary diagram showing a projection image represented by a line projection module of FIG. 1.

In orthopedic surgeries, surgery is often performed after identifying the condition of a bone using a mobile C-arm fluoroscopy (hereinafter, C-arm) and making a surgical plan for cutting and reshaping of the bone. Currently, to this end, a k-wire (a stainless-steel wire) is placed in an affected part, a C-arm image is captured, and a surgical plan is made taking into account the positions of the bone and the k-wire.

A laser targeting projector is used to mark planned lines in a C-arm image directly onto an affected part, and the present disclosure proposes a method for spatial calibration between the laser targeting projector and a C-arm necessary to use the laser targeting projector, and a tool therefor.

The laser surgical guidance system 1 (hereinafter, system) according to the present disclosure calibrates a laser targeting projector and a C-arm image using a calibration tool to help to perform a laser surgery precisely and easily.

Referring to FIG. 1, the system 1 according to the present disclosure includes a C-arm 10 to identify a patient's condition and support a surgical plan, and a laser targeting projector 30 to generate a laser 32 and project a line of the surgical plan directly onto an affected part. The system 1 may be mobile or fixed.

The system 1 of the present disclosure may be where software (application) for performing calibration of the laser targeting projector 30 and the C-arm 10 image may be installed and executed, and the configuration of the C-arm 10 and the laser targeting projector 30 may be controlled by the software for performing calibration of the laser targeting projector 30 and the C-arm 10 image, executed in the system 1.

The configuration of the C-arm 10 and the laser targeting projector 30 may be formed as a terminal, or may be formed as separate modules and connected via a wired/wireless network. In another example, the system 1 may be part of a robot system or a robot arm that performs surgical guidance.

The system 1 may be mobile or fixed. The system 1 may have a form of a device, an apparatus, a terminal, equipment, a server or an engine, and may be called by another name.

Referring to FIG. 2, the laser targeting projector 30 is a device that projects particular osteotomy lines and feature points in a C-arm image directly onto an affected part using a laser.

When a user (for example, a surgeon) marks an osteotomy line 34 according to the surgical plan onto an image of leg bone displayed on a display unit, the image showing surgery information is directly displayed on the affected part such that it matches the human body. Additionally, the user may modify, for example, change or delete, the osteotomy line directly marked on the image of bone.

The osteotomy line refers to a line planned when cutting bones for the treatment of fractures or jaw surgeries. Additionally, the osteotomy line may be marked in a line shape as well as various shapes such as a crossing point 36 and a circle 38.

The surgery information that may be directly inputted from the user includes all information that may be reflected on the surgical plan, including the osteotomy line as well as a fixing pin insertion position and insertion pathway, and needle trajectories.

The laser targeting projector 30 may further include an optical apparatus to project the line, a CMOS camera to simulate the C-arm and a sensor to measure the distance from an object. The optical apparatus may include a Galvano-mirror, a MEMS mirror and a diffuser lens. In an embodiment of the present disclosure, a Galvano-mirror may be used for the optical apparatus.

Figure 3:
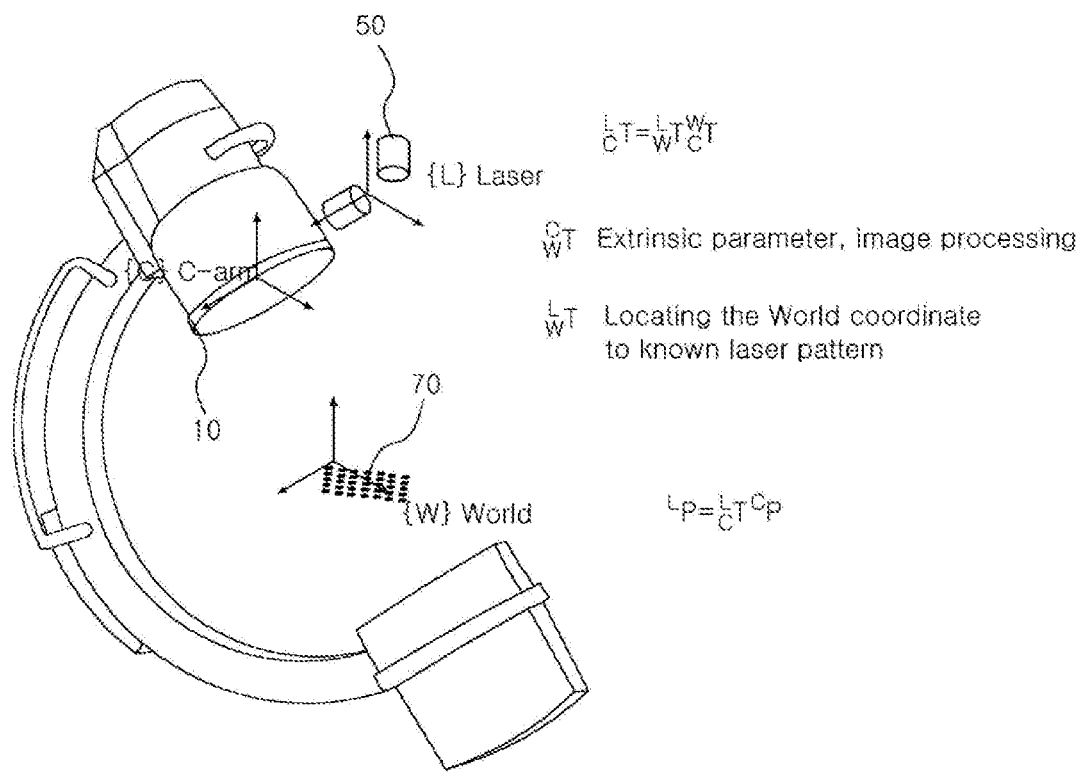
FIG. 3 is a diagram illustrating a spatial calibration algorithm of the present disclosure.

Referring to FIG. 3, the laser targeting projector 30 includes a line projection module 50 to generate a laser, a calibration tool 70 and a calibration unit (not shown).

Figure 4:
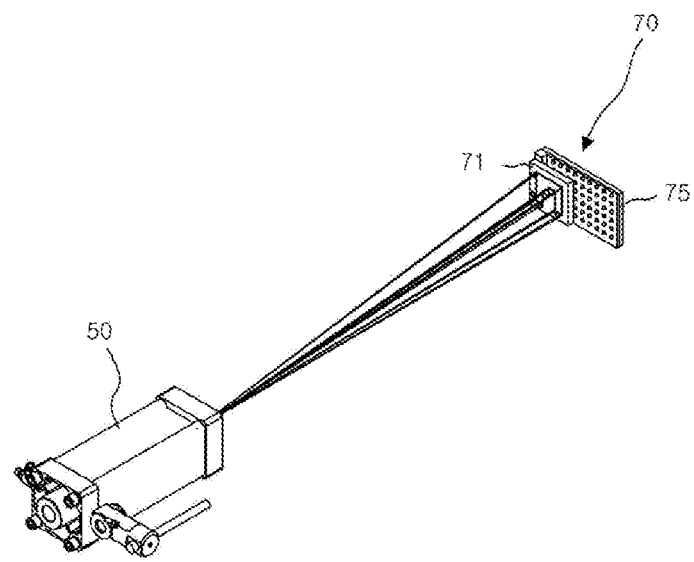
FIG. 4 is a diagram showing a calibration tool according to an embodiment of the present disclosure.
Figure 5A:
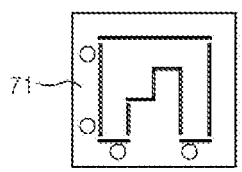
FIG. 5A to FIG. 5D are diagrams showing each part of the calibration tool of FIG. 4 and assembly of the parts.
Figure 5B:
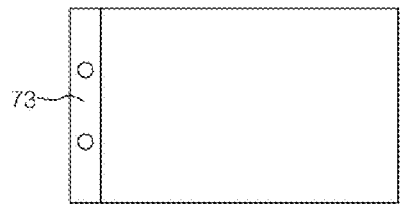
Figure 5C:
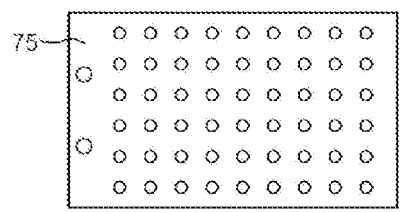
Figure 5D:
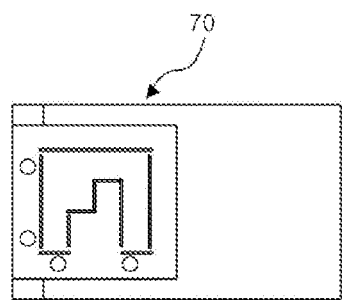

Referring to FIG. 4, the line projection module 50 generates a laser pattern of a particular shape, and the calibration tool 70 is disposed to allow the laser pattern to pass through the calibration tool 70. Additionally, a C-arm 10 image is captured, and the location of a C-arm marker of the calibration tool 70 is calculated, thereby achieving spatial calibration between the C-arm 10 image and the laser targeting projector 30.

The line projection module 50 generates a particular laser pattern, and the calibration tool 70 is spaced apart a predetermined distance from the line projection module, and includes a collimator having a particular orientation for transmitting the particular laser pattern outputted from the line projection module.

The calibration unit calculates the extrinsic parameter of the calibration tool in a projection image having passed through the calibration tool 70, and converts the coordinates of the C-arm image into the line projection module coordinates.

Referring to FIG. 5 (5A to 5D), the calibration tool 70 includes a light pattern matching unit 71 and a C-arm marker unit 75. The calibration tool 70 may further include a screen 73 disposed between the light pattern matching unit 71 and the C-arm marker unit 75.

The light pattern matching unit 71 includes a collimator having a particular orientation for transmitting the particular laser pattern outputted from the line projection module 50.

The pattern of the collimator may be configured under the assumption that the laser beam comes from one point (a pin hole) after being reflected at the Galvanometer. That is, the collimator may be formed in an enlarged pattern having the same shape as the particular laser pattern outputted from the line projection module 50.

The collimator of the light pattern matching unit 71 is formed in an opening pattern, and the opening pattern is formed at a predetermined angle. That is, as shown in FIG. 4, light passes through the collimator obliquely according to the properties of light such as linearity, orientation and scattering.

The screen 73 is a flat screen for seeing the laser pattern having passed through the collimator.

The C-arm marker unit 75 includes bearing balls arranged in a matrix to calculate the extrinsic parameter of the calibration tool 70 so that the laser pattern having passed through the collimator can be recognized in the projection image. In an embodiment, the bearing balls may be made of metal, and may be arranged in a 6×9 matrix.

Referring back to FIG. 3, a spatial calibration algorithm for projecting a particular location on the C-arm image onto the affected part is described.

In each coordinate system for spatial calibration between the C-arm 10 and the line projection module 50, as shown in FIG. 3, {C} denotes the C-arm image coordinate system, {L} denotes the line projection module coordinate system, {W} denotes the calibration tool coordinate system, and when finding $^L_CT$ in the positional relationship of each coordinates, it is possible to convert the coordinates on the C-arm image into points of the line projection module coordinate system.

When expressing this as equation, the following Equation 1 and Equation 2 are given.

$$^L_CT = {}^L_WT \, {}^W_CT \qquad \text{Equation 1}$$

$$^LP = {}^L_CT \, {}^CP \qquad \text{Equation 2}$$

In this instance, is a conversion matrix for converting {b} coordinate system into {a} coordinate system.

When finding $^C_LT$, one point of {C} coordinate system may be expressed as one point of {L} coordinate system.

Here, when it is assumed that the intrinsic parameter of the C-arm 10 is known, $^W_CT$ can be calculated by finding the extrinsic parameter of the calibration tool 70.

$^L_WT$ may be calculated by projecting a preset pattern from the line projection module 50 using a laser and placing the calibration tool 70 at the location. In detail, the laser pattern with the set origin, distance and shape is emitted, and {W} is manually aligned with the pattern.

That is to say, using the set intrinsic parameter of the C-arm and the extrinsic parameter of the calibration tool 70, a conversion matrix between the C-arm image coordinates and the line projection module coordinates is derived. Through this, by matching the coordinates of the origin of the C-arm image coordinates and the line projection module coordinates, the projection image having undergone calibration of the coordinates of the C-arm image and the line projection module coordinates may be accurately projected onto the affected part.

The design of the calibration tool 70 is important to increase the accuracy of and the calibration tool 70 may be designed as shown in FIG. 4 and manufactured as shown in FIG. 5 (5A to 5D) in consideration of linearity of light. However, this is only provided as an example, and modification may be made to the design of the pattern according to the user's needs.

Figure 6:
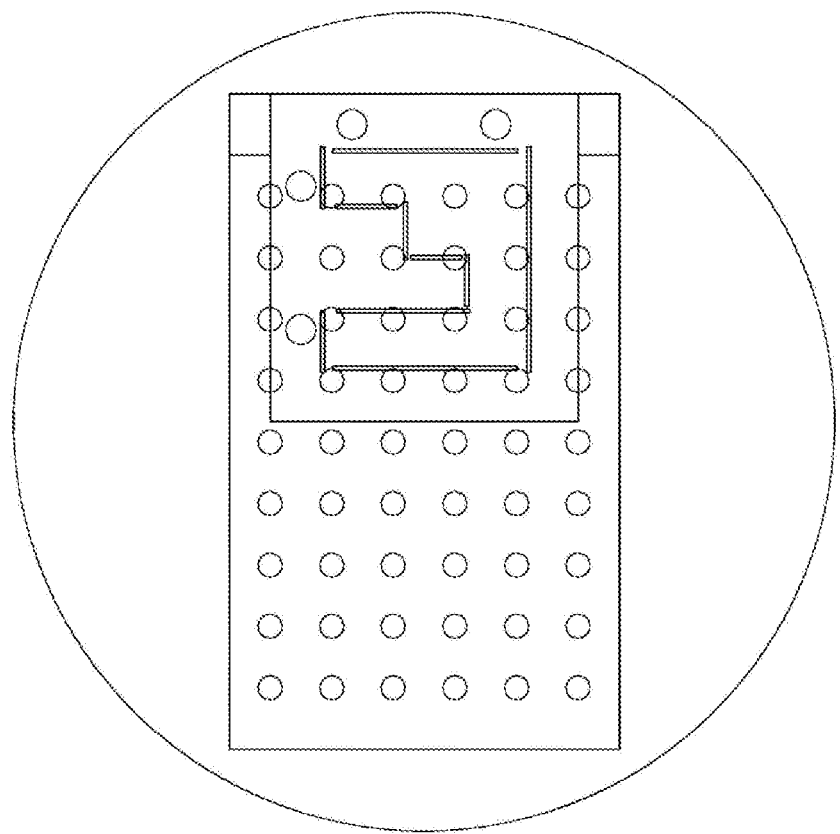
FIG. 6 is a diagram showing a calibration tool scanned by a C-arm.

Referring to FIG. 6, an image of the calibration tool 70 scanned by the C-arm 10 is shown. Additionally, in the laser targeting projection experiment, a test apparatus and environment for testing a quantitative target are created.

The screen is placed at 400 mm distance from the line projection module 50, projection is performed by connecting indicator points designated by a mouse with a laser line in the range of width 150 mm (20 degrees) and height 120 mm (17 degrees), and at this time, a distance error and an angle error are calculated.

Figure 7:
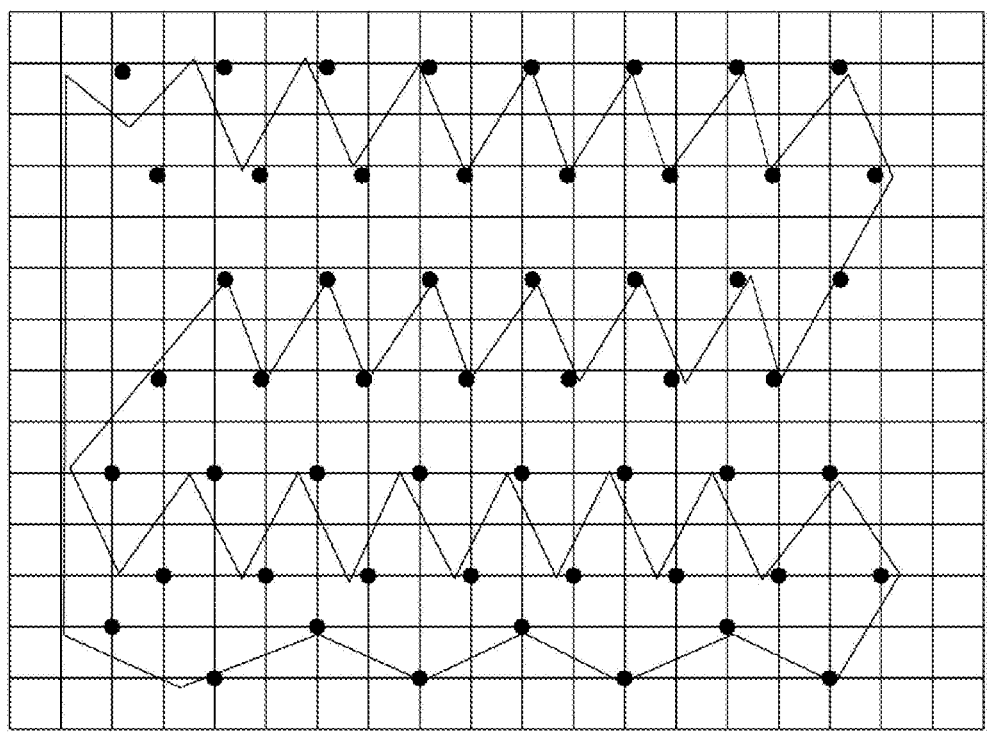
FIG. 7 is a diagram showing the laser projection test result for indicator points in implementing the present disclosure.

In this instance, a laser projected image is shown in FIG. 7. The point is the indicator point, and the line is the laser projection line connecting the indicator points. The point where the projection line turns is a laser projection location corresponding to the indicator point.

Additionally, average distance errors of row and column and maximum/minimum error values are shown in FIG. 8.

Figure 8A:
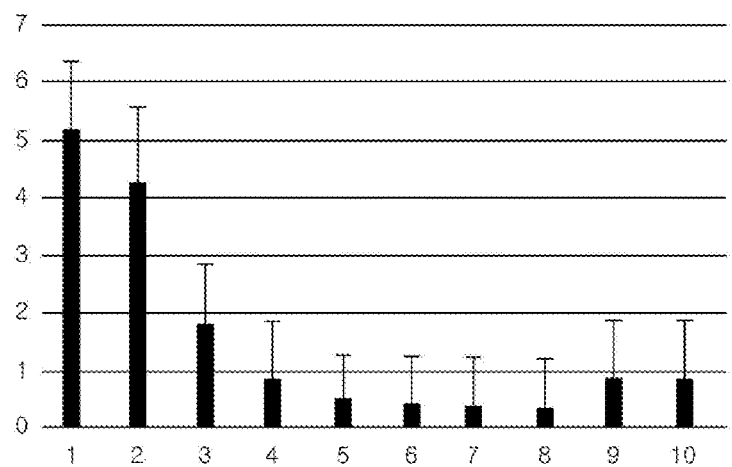
FIG. 8A to FIG. 8B are graphs showing projection precision vs targeting distance in implementing the present disclosure.
Figure 8B:
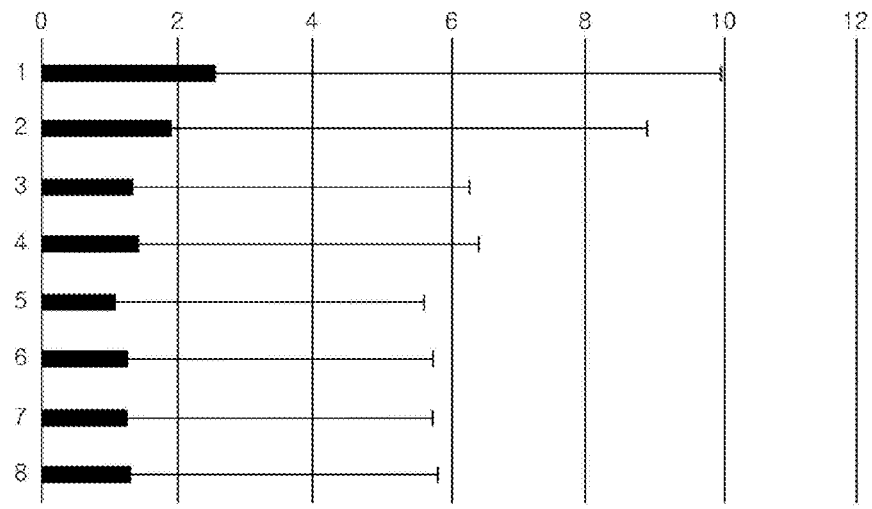

Referring to FIG. 8, it is a diagram showing projection precision vs targeting distance, FIG. 8A shows distance error vs projection column, and FIG. 8B shows distance error vs projection row. A bar indicates an average of distance errors in row/column, and an error bar indicates minimum/maximum values.

An overall average of distance errors is 1.5 mm, a standard deviation is 1.9, and a maximum error value is 7.5 mm. The actually measured angle error is 2° or less. Accordingly, it can be seen that it is possible to achieve precise calibration of the laser targeting projector and the C-arm image according to the present disclosure.

According to the present disclosure, it is possible to indicate a variety of surgery information including osteotomy lines, needle trajectories and pin insertion position and insertion angle, thereby achieving accurate surgery as planned, and reducing the likelihood of surgical errors and medical malpractice. Further, it is possible to achieve quick and accurate surgery according to the imaging plan while reducing the dose of radiation exposure to the surgeon.

Figure 9:
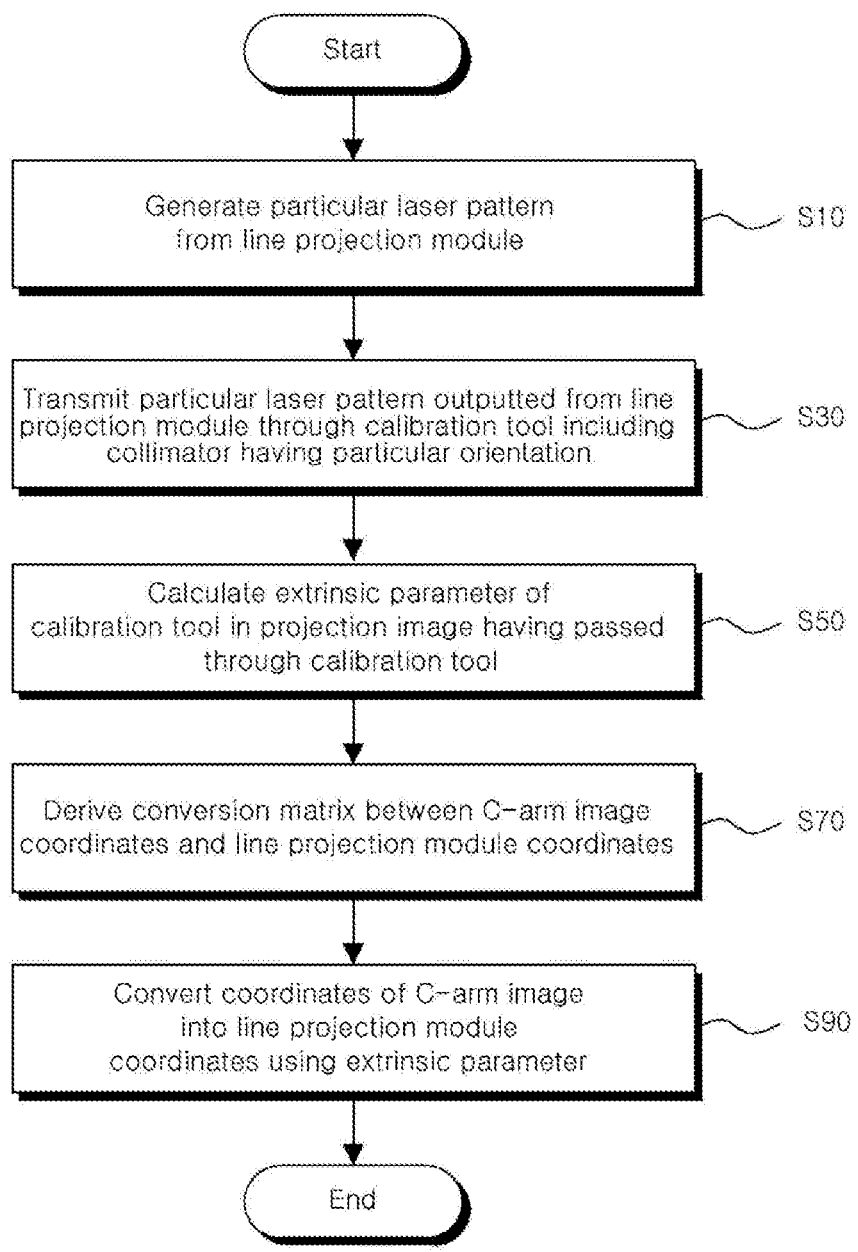
FIG. 9 is a flowchart of a method for calibration of a laser targeting projector and a C-arm image according to an embodiment of the present disclosure.

FIG. 9 is a flowchart of a method for calibration of a laser targeting projector and a C-arm image according to an embodiment of the present disclosure.

The method for calibration of a laser targeting projector and a C-arm image according to this embodiment is performed by a laser surgical guidance system including a C-arm fluoroscopy (hereinafter, C-arm) to identify a patient's condition and support a surgical plan, and a laser targeting projector to project a line of the surgical plan directly onto an affected part through a line projection module that generates a laser.

The method for calibration of a laser targeting projector and a C-arm image according to this embodiment may be performed in substantially the same configuration as the system 1 of FIG. 1. Accordingly, the same element as the system 1 of FIG. 1 is given the same reference sign, and redundant descriptions are omitted herein.

Additionally, the method for calibration of a laser targeting projector and a C-arm image according to this embodiment may be performed by software (application) for performing calibration of the laser targeting projector and the C-arm image.

Referring to FIG. 9, the method for calibration of a laser targeting projector and a C-arm image according to this embodiment includes generating a particular laser pattern from the line projection module 50 S10.

The particular laser pattern generated from the line projection module 50 passes through the calibration tool 70 spaced apart a predetermined distance from the line projection module 50 and including the collimator having the particular orientation S30.

The pattern of the collimator may be configured under the assumption that the laser beam comes from one point (a pin hole) after being reflected at the Galvanometer. That is, the collimator may be formed in an enlarged pattern having the same shape as the particular laser pattern outputted from the line projection module.

The collimator of the light pattern matching unit 71 is formed in an opening pattern, and the opening pattern is formed at a predetermined angle. That is, as shown in FIG. 4, light passes through the collimator obliquely according to the properties of light such as linearity, orientation and scattering.

The laser pattern having passed through the collimator of the calibration tool 70 is displayed on the C-arm marker unit 75 having the bearing balls arranged in a matrix via the screen. The bearing balls may be made of metal so that it can be recognized by the C-arm 10, and may be arranged in a 6×9 matrix.

The laser pattern having passed through the collimator can be recognized by the C-arm 10, and using this, the extrinsic parameter of the calibration tool 70 is calculated by the C-arm marker unit 75 (S50).

The coordinates of the C-arm image are converted into line projection module coordinates using the extrinsic parameter calculated in S50 (S90). To this end, first, a conversion matrix between the C-arm image coordinates and the line projection module coordinates may be derived using the preset intrinsic parameter of the C-arm and the extrinsic parameter of the calibration tool (S70).

Specifically, the spatial calibration algorithm for projecting a particular location on the C-arm image onto the affected part is described above. Accordingly, it is possible to provide precise laser guidance by projecting a projection image having undergone calibration of the coordinates of the C-arm image and the line projection module coordinates directly onto the affected part.

The method for calibration of a laser targeting projector and a C-arm image may be implemented as an application or in the form of program commands that may be executed through various computer components and may be recorded in computer-readable recording media. The computer-readable recording media may include program commands, data files and data structures, alone or in combination.

The program commands recorded in the computer-readable recording media may be specially designed and configured for the present disclosure, and may be those known and available to those having ordinary skill in the field of computer software.

Examples of the computer-readable recording media include hardware devices specially designed to store and execute program commands, for example, magnetic media such as hard disk, floppy disk and magnetic tape, optical media such as CD-ROM and DVD, magneto-optical media such as floptical disk, and ROM, RAM and flash memory.

Examples of the program command include machine code generated by a compiler as well as high-level language code that can be executed by a computer using an interpreter. The hardware device may be configured to act as one or more software modules to perform the processing according to the present disclosure, or vice versa.

While the present disclosure has been hereinabove described with reference to the embodiments, it will be appreciated by those having ordinary skill in the technical field pertaining to the present disclosure that various modifications and changes may be made thereto without departing from the spirit and scope of the present disclosure defined in the appended claims.

INDUSTRIAL APPLICABILITY

The present disclosure can be used in various fields of surgeries using C-arms and is easy to enter the market due to the low medical equipment grade. Additionally, it is possible to directly manufacture/sale in the form of a module in existing C-arms, and enter the market by technology transfer to C-arm manufacturing companies.

The invention claimed is:

1. A laser surgical guidance system comprising:
a C-arm fluoroscopy (C-arm) identifying a patient's condition and supporting a surgical plan, and
a laser targeting projector projecting a line of the surgical plan directly onto an affected part, the laser targeting projector comprising:
a line projector generating a laser;
a calibration tool spaced apart a predetermined distance from the line projector, and including a collimator having a particular orientation for transmitting a particular laser pattern outputted from the line projector; and
a calibrator which calculates an extrinsic parameter of the calibration tool in a projection image having passed through the calibration tool, and converts coordinates of the C-arm image into the line projector coordinates,
wherein the calibration tool comprises:
a light pattern matching unit including the collimator having the particular orientation for transmitting the particular laser pattern outputted from the line projector; and
a C-arm marker unit including bearing balls arranged in a matrix to calculate the extrinsic parameter of the calibration tool, wherein the laser pattern having passed through the collimator is recognizable in the projection image.

2. The laser surgical guidance system according to claim 1, wherein the collimator of the light pattern matching unit is formed in an opening pattern, and the opening pattern is formed at a predetermined angle.

3. The laser surgical guidance system according to claim 1, wherein the calibration tool further includes a screen disposed between the light pattern matching unit and the C-arm marker unit to check the laser pattern having passed through the collimator.

4. The laser surgical guidance system according to claim 1, wherein the bearing balls are arranged in a 6×9 matrix.

5. The laser surgical guidance system according to claim 1, wherein the calibrator derives a conversion matrix between the C-arm image coordinates and the line projector coordinates using a preset intrinsic parameter of the C-arm and the extrinsic parameter of the calibration tool.

6. The laser surgical guidance system according to claim 1, wherein the calibrator matches the coordinates of origin of the C-arm image coordinates and the line projector coordinates.

7. The laser surgical guidance system according to claim 1, wherein the line projector further includes at least one of an optical apparatus to project the line, a CMOS camera to simulate the C-arm, and a sensor to measure a distance from an object.

8. The laser surgical guidance system according to claim 7, wherein the optical apparatus includes at least one of a Galvano-mirror, a micro electro mechanical system (MEMS) mirror, and a Diffuser lens.

9. A calibration tool for performing a method for calibration of a laser targeting projector projecting a line of the surgical plan directly onto an affected part, and a C-arm image, the calibration tool comprising:
- a light pattern matching unit spaced apart a predetermined distance from the laser targeting projector, and including a collimator having a particular orientation for transmitting a particular laser pattern outputted from the laser targeting projector;
- a screen for checking the laser pattern having passed through the collimator; and
- a C-arm marker unit including bearing balls arranged in a matrix to calculate an extrinsic parameter, wherein the laser pattern having passed through the screen is recognizable by a C-arm fluoroscopy (C-arm),
- wherein the calibration tool converts coordinates of the C-arm image into the line projector coordinates.

10. The calibration of claim 9, wherein the collimator of the light pattern matching unit is formed in an opening pattern, and the opening pattern is formed at a predetermined angle.

11. The calibration tool of claim 9, wherein the bearing balls are arranged in a 6×9 matrix.

12. A method for calibration of a laser targeting projector and a C-arm image in a laser surgical guidance system, wherein the laser surgical guidance system comprises a C-arm fluoroscopy (C-arm) identifying a patient's condition and supporting a surgical plan; and the laser targeting projector projecting a line of the surgical plan directly onto an affected part through a line projector which generates a laser, the method comprising:
- generating a particular laser pattern from the line projector;
- transmitting the particular laser pattern outputted from the line projector through a calibration tool including a collimator having a particular orientation;
- calculating an extrinsic parameter of the calibration tool in a projection image having passed through the calibration tool; and
- converting coordinates of the C-arm image into the line projector coordinates using the extrinsic parameter,
- wherein in the calculating the extrinsic parameter, the calibration tool includes bearing balls arranged in a matrix to calculate the extrinsic parameter of the calibration tool, and
- wherein the particular laser pattern having passed through the collimator is recognizable in the projection image.

13. The method of claim 12, wherein the step of the converting comprises deriving a conversion matrix between the C-arm image coordinates and the line projector coordinates using a preset intrinsic parameter of the C-arm and the extrinsic parameter of the calibration tool.

14. The method of claim 12, wherein the step of the converting comprises matching the coordinates of origin of the C-arm image coordinates and the line projector coordinates.

15. The method of claim 12, further comprising:
- projecting the projection image having undergone calibration of the coordinates of the C-arm image and the line projector coordinates directly onto the affected part.

16. A non-transitory computer-readable recording medium having recorded thereon a computer program for performing the method for calibration of a laser targeting projector and a C-arm image according to claim 12.

* * * * *